United States Patent
Camy et al.

(10) Patent No.: US 8,779,363 B2
(45) Date of Patent: Jul. 15, 2014

(54) CHEMICAL SPECIES OPTICAL SENSOR OPERATING IN INFRARED

(75) Inventors: Patrice Camy, Caen (FR); Jean-Louis Doualan, Rots (FR); Virginie Nazabal, Rennes (FR)

(73) Assignee: Centre National de la Recherche Scientifique, Paris (FR)

( * ) Notice: Subject to any disclaimer, the term of this patent is extended or adjusted under 35 U.S.C. 154(b) by 204 days.

(21) Appl. No.: 13/500,858

(22) PCT Filed: Oct. 8, 2010

(86) PCT No.: PCT/FR2010/000679
§ 371 (c)(1),
(2), (4) Date: Jun. 7, 2012

(87) PCT Pub. No.: WO2011/042628
PCT Pub. Date: Apr. 14, 2011

(65) Prior Publication Data
US 2012/0241623 A1    Sep. 27, 2012

(30) Foreign Application Priority Data
Oct. 8, 2009 (FR) ..................................... 09 04809

(51) Int. Cl.
| G01N 21/3504 | (2014.01) |
| G01N 33/00 | (2006.01) |
| G01N 21/63 | (2006.01) |
| G01N 21/31 | (2006.01) |
| G01N 21/35 | (2014.01) |

(52) U.S. Cl.
CPC ............ *G01N 33/004* (2013.01); *G01N 21/636* (2013.01); *G01N 21/314* (2013.01); *G01N 21/3504* (2013.01)
USPC .................................................. 250/339.13

(58) Field of Classification Search
CPC ................. G01J 1/42; G01J 1/58; G01J 3/10; G01N 21/35; G01N 21/64; G01N 21/75; G01N 21/314; G01N 21/3504; G01N 21/636; G01N 33/004; G01N 2021/3166; G01N 2021/3185; G01N 2021/3513; G01N 2021/084; G01N 33/00
USPC ............. 250/338.1, 338.5, 339.01, 339.06, 250/339.12, 339.13, 361 R, 338.3, 458.1, 250/459.1, 330–395
See application file for complete search history.

(56) References Cited

U.S. PATENT DOCUMENTS

| 6,114,700 A | 9/2000 | Blades |
| 7,049,622 B1 * | 5/2006 | Weiss ............................ 250/577 |

(Continued)

FOREIGN PATENT DOCUMENTS

| FR | 2 771 405 | 5/1999 |
| GB | 2 102 942 | 2/1983 |
| WO | WO 99/13303 | 3/1999 |
| WO | WO 9913303 A1 * | 3/1999 |

OTHER PUBLICATIONS

International Search Report for PCT/FR2010/000679 Dated Dec. 22, 2010.

(Continued)

*Primary Examiner* — David Porta
*Assistant Examiner* — Adam J Fifth
(74) *Attorney, Agent, or Firm* — B. Aaron Schulman, Esq.; Stites & Harbison, PLLC.

(57) ABSTRACT

The invention relates to a chemical species optical sensor comprising: a fluorescent source (3) of incoherent infrared rays, including a chalcogenide glass matrix, doped with rare earth ions and combined with a pump source by means of a first optical fiber (2); and at least one infrared ray detector (5), provided with a spectral selection device (50) and set up to detect the rays that are emitted by said fluorescent source and have passed through a detection area (6), said detector including a fluorescent element (510) formed by a chalcogenide glass matrix that is doped with rare earth ions and combined with a second pump source (530) by means of a second optical fiber (520). Such a sensor can be used for differentially detecting a chemical species, and in particular $CO_2$.

19 Claims, 2 Drawing Sheets

(56) References Cited

U.S. PATENT DOCUMENTS

| | | | |
|---|---|---|---|
| 7,425,452 B2 * | 9/2008 | Kajii | 436/135 |
| 2005/0269499 A1 | 12/2005 | Jones | |
| 2007/0279633 A1 | 12/2007 | Yi et al. | |
| 2009/0274420 A1 * | 11/2009 | Vallee et al. | 385/37 |

OTHER PUBLICATIONS

Written Opinion of the International Searching Authority for PCT/FR2010/000679, Dec. 30, 2010.

I.D. Aggarwal, J.S. Sanghers: "Development and applications of chalcogenide glass optical fibers at nrl", Journal of Optoelectronics and Advanced Material, vol. 4, No. (Sep. 2002), pp. 665-678.

Schweizer T et al: "Spectroscopic Data of the 1.8-, 2.9-, and 4.3MUM Transitions in Dysprosium-Doped Gallium Lanthanum Sulfide Glass", Optics Letters, OSA, Optical Society of America, Washington, DC, US, vol. 21, No. 19, (Oct. 1, 1996), pp. 1594-1596.

Mitsunori Saito et al: "CO2 Gas Sensor Using Acousto-Optic Bragg Diffraction in AS2SE3 Glass", Review of Scientific Instruments, AIP, Melville, NY, US LNKD D01:10.1063/1.1142374, vol. 62, No. 9, (Sep. 1, 1991), pp. 2105-2108.

* cited by examiner

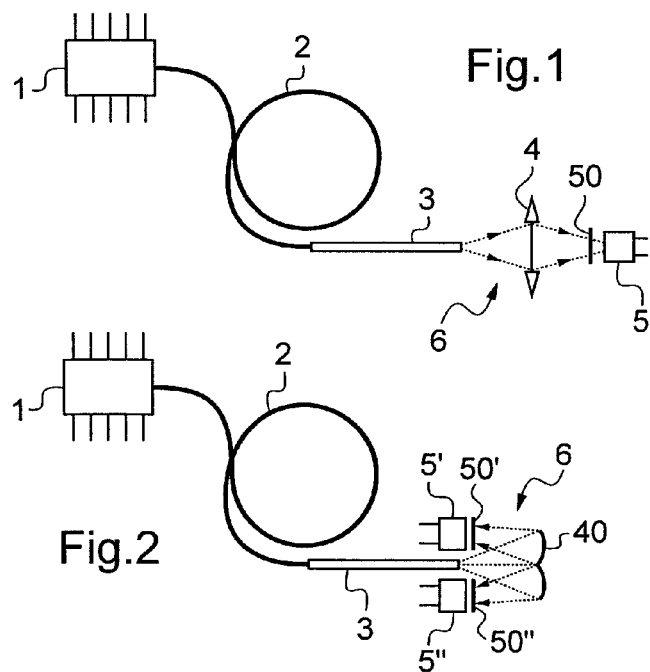
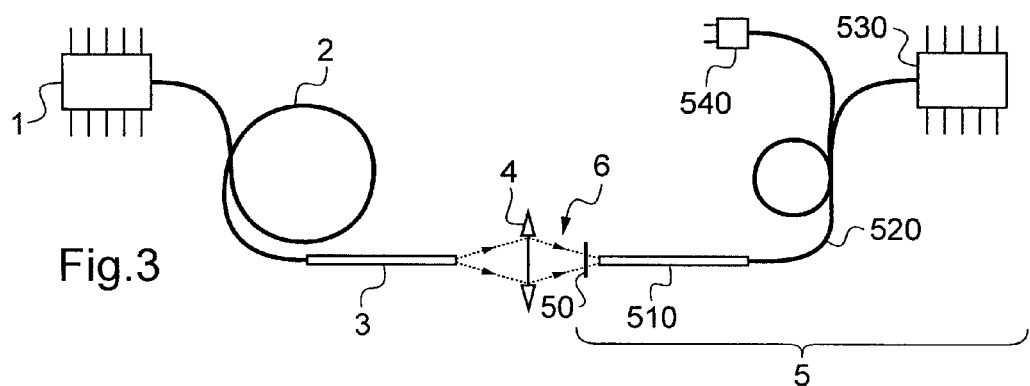
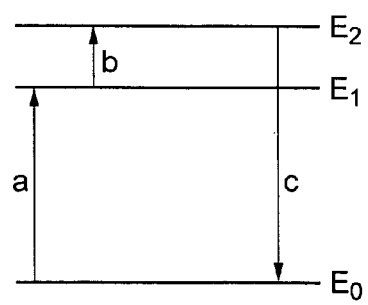

CHEMICAL SPECIES OPTICAL SENSOR OPERATING IN INFRARED

The invention relates to a chemical sensor of optical species, in particular gaseous species, the sensor operating in the infrared and more particularly in the mid-infrared (2 micrometers (μm) to 5 μm). The invention also relates to a method of detecting chemical species, and in particular gaseous $CO_2$, optically—and more precisely by spectroscopy.

Numerous chemical species can be detected by measuring their absorption in the infrared, and more specifically in the mid-infrared, i.e. at wavelengths lying in the range approximately 2 μm to 5 μm. Detection may advantageously be performed in differential manner, i.e. by measuring the spectral intensity at two different wavelengths of infrared radiation that has passed through a detection region containing the chemical species that is to be detected.

The infrared radiation used for detection may be generated by a thermal source of the black body type: see for example documents US 2007/0279633 and U.S. Pat. No. 6,114,700. Sources of that type are generally not very satisfactory because of their low brightness, because of the difficulty experienced in focusing the radiation they emit, and because of the excessive width of their emission spectrum compared with the useful spectrum band.

Charpentier et al. [1] have proposed making an optical sensor of gaseous $CO_2$ by using a remote thermal type infrared source. In that sensor, the detection region (which may be a geological reservoir or any other environment that is hostile for electrical or electronic equipment) is at a distance from the source, with infrared radiation being transported thereto by an optical fiber made of chalcogenide glass: this is because the optical fibers that are in most widespread use are made of $SiO_2$, and they are not transparent at wavelengths longer than about 2 μm. Optical fibers made of fluorides also present a cutoff wavelength that is too short. The radiation detector for measuring the spectral intensity of the radiation after it has passed through the detection region may also be remote, and may be coupled to said detection region by a second optical fiber made of chalcogenide glass. The drawback of that system is that optical fibers made of chalcogenide glass present a relatively high level of attenuation, of the order of 0.1 decibels per meter (dB/m) to 1 dB/m, thereby making worse the above-mentioned drawbacks of thermal type infrared sources ([2,3]).

In practice, the remoteness of the light source is thus restricted to no more than about ten meters.

It is also known (from US 2005/0269499) to use light-emitting diodes (LEDs) as sources of infrared radiation in optical sensors of chemical species. The spectrum of the radiation emitted by such LEDs varies greatly with temperature, which makes differential detection difficult and unreliable.

Proposals have also been made to use lasers. The active medium of lasers that emit in the mid-infrared may comprise rare earth ions in a chalcogenide glass matrix, possibly in the form of an optical fiber: see for example [4]. Such lasers are complex to implement and expensive.

The document WO 99/13303 and the article by I. D. Aggarwal and J. S. Sanghers "Development and applications of chalcogenide glass optical fibers at NRL", Journal of Optoelectronics and Advanced Materials, Vol. 4, No. 3, September 2002, pp. 665-678, disclose a doped chalcogenide glass element that is optically pumped for use as a source of incoherent infrared radiation for spectroscopic detection of $CO_2$. Neither the pumping source nor the infrared radiation detector can be located remotely.

The invention seeks to provide an optical sensor and a method of optically detecting chemical species, in particular gaseous $CO_2$, that do not present the above-mentioned drawbacks of the prior art.

In accordance with a first aspect of the invention, this object may be achieved by an optical sensor of chemical species comprising: a fluorescent source 3 of incoherent infrared radiation comprising a chalcogenide glass matrix doped by rare earth ions; at least one infrared radiation detector 5 or 5' and 5" provided with a spectrum selector device 50 or 50' and 50" and arranged to detect the radiation emitted by said fluorescent source 3, a chemical species detection zone 6 being provided between said source 3 and said detector 5; and a pumping source 1 emitting visible or infrared radiation adapted to excite the fluorescence of said rare earth ions. Typically, the pumping source 1 may be a semiconductor laser emitting in the visible or in the near infrared (wavelength shorter than 1 μm).

This device differs from those known in the prior art mainly by the fact that it uses a source of incoherent infrared radiation relying on the fluorescence of rare earth ions dispersed in a chalcogenide glass matrix. Such a source presents brightness that is much greater than that of conventional thermal sources. Its emission spectrum is wide enough to enable target chemical species to be detected differentially without being excessively wide, as the spectrum is with thermal sources. Unlike LEDs, such a source is very insensitive to ambient temperature variations, so long as the temperature remains below the glass transition temperature, typically about 200° C. to 350° C., depending on the composition of the matrix, and such a source is much simpler to implement than an infrared laser.

Advantageously, the sensor may also include an optical fiber 2 coupling said pumping source 1 to said fluorescent source 3 in such a manner as to enable them to be separated in space. The pumping source 1 may thus be remote from the potentially hostile environment in which the measurement is performed. Whereas Charpentier et al. [1] propose having the infrared source itself located remotely, with the radiation being transported by a chalcogenide glass fiber, the invention proposes having only the pumping source 1 located remotely, with the infrared radiation being generated in situ by a technique that is purely optical. The major advantage is that the pumping radiation can be transported by a conventional optical fiber 2 that is made of silica with light losses that are very low, thus enabling the source to be located remotely at a distance of several hundreds of meters (m), or even further. The fluorescent source 3 of infrared radiation does not need to be located remotely: it is a device that is purely optical, that is insensitive to electromagnetic disturbances, and that can withstand temperatures that are relatively high, as explained above.

In various embodiments of the invention:

Said infrared radiation detector 5 may be provided with a tunable spectrum selector device 50 enabling the spectral intensity of the infrared radiation that has passed through the chemical species detection zone 6 to be measured at at least two different wavelengths.

In a variant, the sensor may include at least two said infrared radiation detectors 5', 5", each provided with a spectrum selector device 50', 50" tuned to a different wavelength.

The chalcogenide glass matrix of said fluorescent source of infrared radiation may be of the Ge—Ga(In)—(Sb)—(CsI)—S(Se,Te) type, doped by trivalent ions of at least one rare earth at a concentration greater than or equal to 500 parts per million (ppm), and preferably lying in the range 1000 ppm to 3000 ppm.

The chalcogenide glass matrix of said fluorescent source 3 of infrared radiation may be doped with $Dy^{3+}$ or $Pr^{3+}$ ions at a concentration greater than or equal to 500 ppm, and preferably lying in the range 1000 ppm to 3000 ppm, whereby said fluorescent source 3 of in infrared radiation emits radiation at 4.3 µm.

Said fluorescent source 3 of infrared radiation may present emission with a spectrum width at half maximum lying in the range 200 nanometers (nm) to 800 nm.

Said fluorescent source 3 of infrared radiation may be in the form of a waveguide, and preferably of an optical fiber. This makes it possible to increase the brightness of the source and makes it easier to focus the emitted radiation on the detector 5.

In a preferred embodiment of the invention, the infrared radiation detector 5 is also located remotely. Once more, transporting infrared radiation over long distances is avoided, since that would give rise to high losses that would degrade the sensitivity of detection. A fluorescent element 510 (chalcogenide glass matrix doped with rare earth ions) pumped by visible or near-infrared radiation serves to convert radiation photons to higher energies, thereby enabling them to be transported using a conventional optical fiber 520 all the way to a remote detector 540. The detector 5, which thus operates at shorter wavelengths, may be much more efficient than detectors that are sensitive in the mid-infrared. More precisely, in such a preferred embodiment of the invention, said infrared radiation detector 5 comprises:

a fluorescent element 510 arranged to be illuminated by the infrared radiation emitted by said source 1 after passing through said chemical species detection zone 6, said fluorescent element 510 comprising a rare earth ion doped chalcogenide glass matrix in which said ions, when in a first excited state, are capable of absorbing a photon of said radiation, and then of emitting a photon at a shorter wavelength;
 a second pumping source 530 emitting visible or infrared radiation adapted to take said rare earth ions into said first excited state; and
 a second optical fiber 520 coupling said fluorescent element 510 to a radiation detector 540, so as to enable them to be physically spaced apart.

Such a sensor may also include a second infrared radiation detector 540" that comprises: a second fluorescent element 510" arranged to be illuminated by the infrared radiation emitted by said source 1 after passing through said chemical species detection zone 6, said fluorescent element 510" comprising a rare earth ion doped chalcogenide glass matrix in which said ions, when in a first excited state, are capable of absorbing a photon of said radiation, and then of emitting a photon at a shorter wavelength; a third pumping source 530" emitting visible or infrared radiation adapted to take said rare earth ions into said first excited state; and a third optical fiber 520" coupling said fluorescent element 510" to a second radiation detector 540"; each of said two infrared radiation detectors 540', 540" being provided with a respective spectrum selector device 50", 50" tuned to a different wavelength in order to filter the incident infrared radiation on the respective fluorescent element 510', 510".

Said or each fluorescent element 510 or 510' and 510" may be coupled to its pumping source 530 or 530' and 530" by a respective optical fiber 520 or 520' and 520".

Advantageously, the chalcogenide glass matrix of said fluorescent source 510 or 510' and 510" of infrared radiation may be doped with $Dy^{3+}$ or $Pr^{3+}$ ions, whereby said source 530 or 530' and 530" emits radiation at 4.3 µm; and the chalcogenide glass matrix of said or each fluorescent element 510 or 510' and 510" of the sensor may be doped with $Er^{3+}$ ions.

Said or each fluorescent element 510 or 510' and 510" may be in the form of a waveguide, and preferably of an optical fiber.

The or each optical fiber 520 or 520' and 520" connecting said or each fluorescent element 510 or 510' and 510" to the pumping source 530 or 530' and 530" and to the respective radiation detector 540 or 540' and 540" may be a silicon fiber.

The invention also provides a method of detecting a chemical species by measuring the absorption at at least two distinct wavelengths of incoherent infrared radiation emitted by fluorescence from rare earth ions in a chalcogenide glass matrix, the method being characterized by the use of a sensor of chemical species as described above.

Advantageously:
 said incoherent infrared radiation may present a spectrum width at half maximum lying in the range 200 nm to 800 nm, and a wavelength of 4.3 µm; and
 said chemical species may be gaseous $CO_2$.

Other characteristics, details, and advantages of the invention appear on reading the following description made with reference to the accompanying drawings given by way of example and in which:

FIG. 1 shows a first embodiment of an optical sensor of chemical species;

FIG. 2 shows a second embodiment of an optical sensor of chemical species;

FIG. 3 shows a third embodiment of an optical sensor of chemical species;

FIG. 4 is an energy level diagram showing the conversion to higher energies of infrared photons as implemented in the FIG. 3 sensor;

Figure 5:
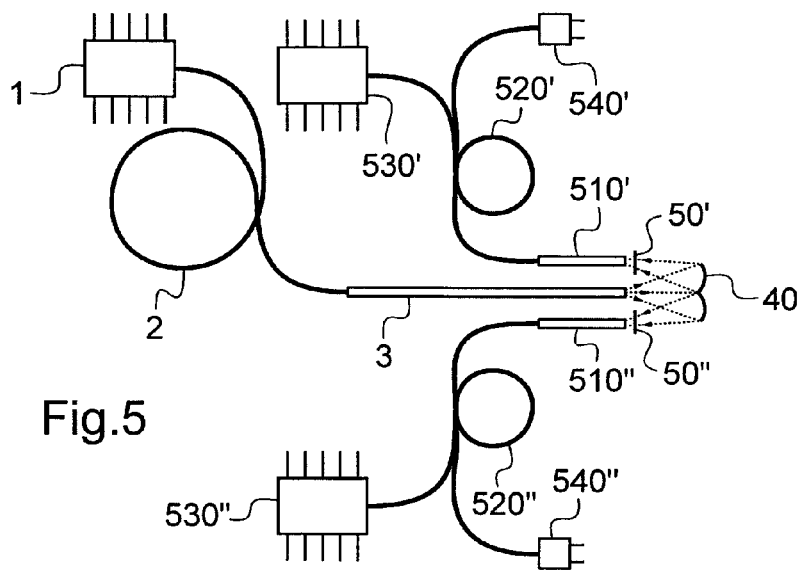
FIG. 5 shows an optical sensor of chemical species in a fourth embodiment of the invention.

The FIG. 1 sensors comprises an infrared radiation source in the form of an optical fiber 3 of chalcogenide glass that is doped with rare earth ions, in particular trivalent ions. The length of the fiber may be a few centimeters (cm), e.g. lying in the range 1 cm to 20 cm.

Broadly speaking, a chalcogenide is a chemical compound consisting of at least one chalcogen atom other than oxygen and at least one atom of an element that is more electropositive. The chalcogens are the elements of group 16 in the periodic table, namely: O, S, Se, Te, and Po. Oxides are not considered as being chalcogenides. Chalcogenide glasses are amorphous materials constituted by chalcogenides. They are characterized by being transparent in the infrared, and for this reason they are used for making optical fibers that operate in this region of the spectrum. It is known to dope chalcogenide glasses with rare earths, which present fluorescent emission in the region in which these materials are transparent.

Reference [2] describes in general manner the properties and applications of chalcogenide glasses.

References [3] and [5] deal more specifically with optical fibers made of rare earth doped chalcogenide glasses.

Document FR 2 771 405 discloses chalcogenide glass compositions presenting optical properties that are particularly favorable.

The optical fiber 3 may be made of a chalcogenide glass of the Ge—Ga(In)—(Sb)—(CsI)—S(Se,Te) type, where the elements in parentheses may be present or absent. In the example of FIG. 1, said fiber is made of $Ge_5Ga_{20}Sb_{10}S_{65}$ that is doped with $Dy^{3+}$ ions at a concentration greater than 500 ppm and preferably at a concentration lying in the range 1000 ppm to 3000 ppm. A level of concentration that is that high makes it possible to provide a radiation source that is particularly compact [6]. It is also possible to use $Pr^{3+}$ ions as a replacement for $Dy^{3+}$.

When pumped optically at 920 nm, the fiber 3 emits fluorescence that presents a peak at 4.3 µm with a bandwidth of about 250 nm. This is particularly suitable for detecting gaseous $CO_2$ which specifically presents an absorption peak at 4.3 µm.

The fiber 3 is pumped at 920 nm by a semiconductor laser 1. Advantageously, the laser is remote and coupled to the chalcogenide glass optical fiber 3 via the first optical fiber 2 that is of "conventional" type, and typically made of silica. The fiber 2 presents losses that are extremely low, and may therefore have a length of several tens or several hundreds of meters or even several kilometers (km).

The infrared radiation emitted by the fiber 3 passes through a detection zone 6 that contains the chemical species to be detected (e.g. $CO_2$), and is then focused by a lens 4 onto a radiation detector 5. The lens 4 is made of a material that is transparent in the infrared: chalcogenide, $CaF_2$, ZnSe, sapphire; it could be replaced by a concave mirror.

The detector 5, of PbSe photoconductor or pyroelectrical type, is fitted with a tunable spectral filter 50 (e.g. the LFP-3950L-337 filter from Infratec). By acting on the spectral filter 50, it is possible to measure the spectral intensity of the incident radiation on the detector 5 at two (or more) different wavelengths. Using the principle of differential spectral detection, this makes it possible to determine the concentration of an absorbent chemical species inside the zone 6.

FIG. 2 shows a sensor in a second embodiment of the invention comprising two infrared detectors 5', 5" and two respective interference filters 50', 50" that are passive (i.e. not tunable), and transparent at different wavelengths. The radiation from the fiber 3 is focused on these sensors by a pair of concave mirrors 40.

FIG. 3 shows another embodiment of the sensor of the invention, enabling nearly all of the electrical, electronic, or optoelectronic components, including those used for picking up the infrared radiation that has passed through the detection region 6, to be located remotely. In this sensor, the detector 5 operates on the principle of converting infrared photons towards higher energies. The lens 4 focuses the infrared radiation as filtered by the tunable filter 50 onto a second chalcogenide glass optical fiber 510 that is doped with rare earth ions. When in a first excited state of energy $E_1$, these ions are capable of absorbing a photon of the radiation in order to reach a second excited state of energy $E_2$. Thereafter they return to the fundamental state $E_0$ while emitting a photon that is visible or in the near infrared (e.g. having a wavelength longer than 1 µm). This is shown in FIG. 4, where a indicates pumping from level $E_0$ to level $E_1$, b indicates absorption of an infrared photon, and c indicates spontaneous emission of a visible or near-infrared photon.

By way of example, the chalcogenide glass optical fiber 510 may be doped with $Er^{3+}$ ions and may be pumped at 980 nm.

The pumping radiation emitted by the semiconductor laser 530 is conveyed to the chalcogenide glass fiber 510 by a conventional optical fiber 520, referred to as the "second" optical fiber. This same optical fiber 520, or a separate fiber, is also used for conveying the radiation emitted by $E_2$–$E_1$ fluorescence to a detector 540. The laser 530 and the detector 540 may thus be located remotely. Another advantage of this scheme is that the detector 540 that is sensitive in the near infrared (or in the visible) may present efficiency that is greater than that of the detector 5 for mid-infrared. The transition band b must be sufficiently wide and must overlap the emission band of the fiber 3 sufficiently to make differential detection possible for the chemical species contained in the zone 6.

The filter 50 is of the tunable type, and may be situated in front of the fiber 510 as shown in the Figure. It is not possible to locate it immediately in front of the detector 540 since the frequency conversion destroys the spectral information. This tunable filter 50 thus remains the only electrical/electronic component of the detector 540 that cannot be located remotely.

Two possibilities exist for genuinely locating all of the electrical elements of the detector 540 remotely.

The first consists in using a (non-tunable) passive filter instead of the tunable filter 50. This involves measuring spectral intensity at a single wavelength, and thus not being able to perform differential detection. Nevertheless, this solution presents the advantage of simplicity, and is acceptable when the concentration of chemical species that is to be detected is relatively great, and without there being any need to evaluate said concentration quantitatively.

The second possibility consists in duplicating the frequency conversion system, using two infrared detectors 5', 5", i.e. two fluorescent elements 510', 510", each provided with a respective pumping source 540', 540" (in fact, it is also possible to use a single common pumping source), a respective optical detector 530', 530", and a respective coupling fiber 520', 520". The complexity of such a system nevertheless remains acceptable in most applications, and is shown in FIG. 5.

Figure 6A:
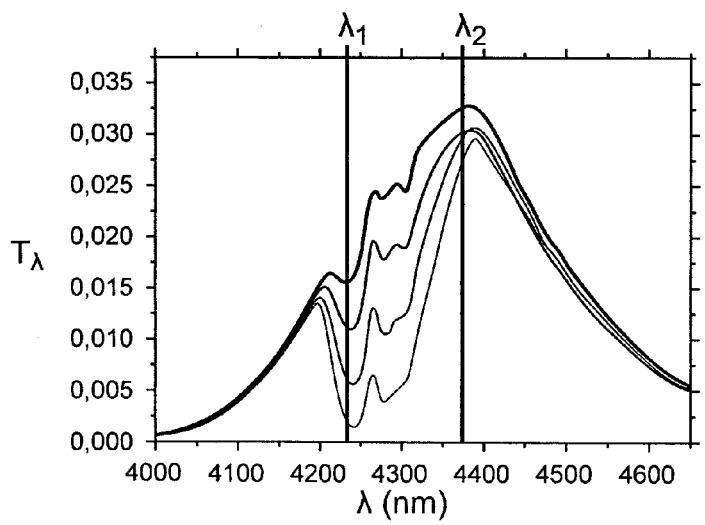
FIGS. 6A and 6B are graphs obtained from experimental measurements showing the use of incoherent infrared radiation emitted by fluorescence from rare earth ions in a chalcogenide glass matrix for optically detecting gaseous $CO_2$.
Figure 6B:
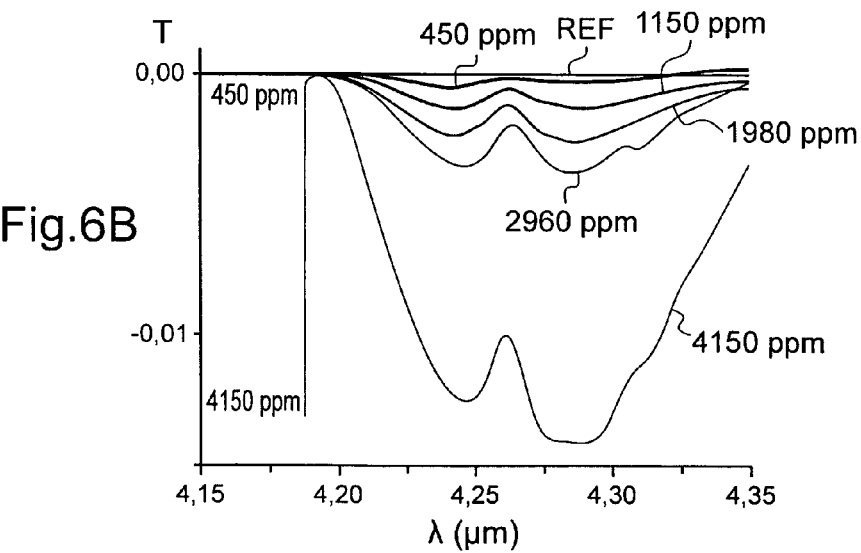

FIG. 6A shows the variation in the spectral intensity $I_\lambda$ of the infrared radiation emitted by the fiber 3 in FIG. 1 after passing through a detection zone 6 having a typical length lying in the range 1 cm to 10 cm (however it is also possible to use longer lengths), and containing a concentration of $CO_2$ that lies in the range 450 ppm to 4150 ppm. FIG. 6B shows the transmittance T as a function of wavelength λ, with this being obtained by comparing the spectra of the infrared radiation that has passed through a detection zone 6 containing $CO_2$ at five different levels of concentration with a spectrum as obtained in the absence of $CO_2$.

It can be seen that the signal-to-noise ratio is excellent.

The spectra of FIG. 6A were obtained using a monochromator. Nevertheless, for detecting $CO_2$, it suffices to measure $I_\lambda$ at two wavelengths $\lambda_1$ and $\lambda_2$; as can be seen in FIG. 6A, the ratio $I_\lambda(\lambda_1)/I_\lambda(\lambda_2)$, and also the difference $I_\lambda(\lambda_2)-I_\lambda(\lambda_1)$ both vary with $CO_2$ concentration, thus making it possible to determine that concentration, after prior calibration.

The invention may also implement integrated optics techniques. Under such circumstances, the optical fibers, whether made of chalcogenide glass or "conventional" glass, or at least some of them, may be replaced by planar waveguides. The use of fluorescent elements that do not form waveguides may also be envisaged, however the use of structures that provide radiation confinement is generally most advantageous.

REFERENCES

[1] Charpentier et al. "Infrared monitoring of underground $CO_2$ storage using chalcogenide glass fibers", Optical Materials, Vol. 31, No. 3, January 2009, pp. 496-500.

[2] D. Lezar "Chalcogenide glasses—survey and progress", Journal of Optoelectronics and Advanced Materials, Vol. 5, No. 1, March 2003, pp. 23-34.

[3] J. S. Shangera et al. "Application of chalcogenide glass optical fibers at NRL", Journal of Optoelectronics and Advanced Materials, Vol. 3, No. 3, September 2001, pp. 627-640.

[4] T. Schweitzer et al. "Fabrication and spectroscopy of erbium doped gallium lanthanum sulphide glass fibres for mid-infrared laser applications", Optics Express, Vol. 1, No. 4, Aug. 18, 1997, pp. 102-107.

[5] B. Cole et al. "Rare-earth doped selenide glasses and fibers for active applications in the near and mid-IR", Journal of Non-Crystalline Solids 256&257 (1999), pp. 253-259.

[6] V. Moizan, "Etude de l'amplification laser en bande II dans les fibres de verres chalcogénures" [Study of band II laser amplification in chalcogenide glass fibers], Thesis, University of Rennes II, Sep. 29, 2008.

The invention claimed is:

1. An optical sensor of chemical species comprising:
   a fluorescent source of incoherent infrared radiation comprising a chalcogenide glass matrix doped by rare earth ions;
   at least one infrared radiation detector provided with a spectrum selector device and arranged to detect the radiation emitted by said fluorescent source, a chemical species detection zone being provided between said source and said detector; and
   a pumping source emitting visible or infrared radiation adapted to excite the fluorescence of said rare earth ions;
   the sensor being characterized in that:
      it also comprises a first optical fiber coupling said pumping source to said fluorescent source;
   and in that said infrared radiation detector comprises:
      a fluorescent element arranged to be illuminated by the infrared radiation emitted by said source after passing through said chemical species detection zone, said fluorescent element comprising a rare earth ion doped chalcogenide glass matrix in which said ions, when in a first excited state, are capable of absorbing a photon of said radiation, and then of emitting a photon at a shorter wavelength;
      a second pumping source emitting visible or infrared radiation adapted to take said rare earth ions into said first excited state; and
      a second optical fiber coupling said fluorescent element to a radiation detector.

2. An optical sensor of chemical species according to claim 1, also including a second infrared radiation detector that comprises:
   a second fluorescent element arranged to be illuminated by the infrared radiation emitted by said source after passing through said chemical species detection zone, said fluorescent element comprising a rare earth ion doped chalcogenide glass matrix in which said ions, when in a first excited state, are capable of absorbing a photon of said radiation, and then of emitting a photon at a shorter wavelength;
   a third pumping source emitting visible or infrared radiation adapted to take said rare earth ions into said first excited state; and
   a third optical fiber coupling said fluorescent element to a second radiation detector;
   each of said two infrared radiation detectors being provided with a respective spectrum selector device tuned to a different wavelength in order to filter the incident infrared radiation on the respective fluorescent element.

3. An optical sensor of chemical species according to claim 1, wherein said or each fluorescent element is coupled to its pumping source by a respective optical fiber.

4. An optical sensor of chemical species according to claim 1, wherein:
   the chalcogenide glass matrix of said fluorescent source of infrared radiation is doped with $Dy^{3+}$ or $Pr^{3+}$ ions, whereby said source emits radiation at 4.3 µm; and
   the chalcogenide glass matrix of said or each fluorescent element of the sensor is doped with $Er^{3+}$ ions.

5. An optical sensor of chemical species according to claim, 1 wherein said or each fluorescent element is in the form of a waveguide.

6. An optical sensor of chemical species according to claim 1, wherein the or each optical fiber connecting said or each fluorescent element to the pumping source and to the respective radiation detector is a silicon fiber.

7. An optical sensor of chemical species according to claim 1, wherein said first optical fiber is a silica fiber.

8. An optical sensor of chemical species according to claim 1, wherein said infrared radiation detector is provided with a tunable spectrum selector device enabling the spectral intensity of the infrared radiation that has passed through the chemical species detection zone to be measured at at least two different wavelengths.

9. An optical sensor of chemical species according to claim 1, including at least two said infrared radiation detectors, each provided with a spectrum selector device tuned to a different wavelength.

10. An optical sensor of chemical species according to claim 1, wherein the chalcogenide glass matrix of said fluorescent source of infrared radiation is of the Ge—Ga(In)—(Sb)—(CsI)—S(Se,Te) type, doped by trivalent ions of at least one rare earth at a concentration greater than or equal to 500 ppm.

11. An optical sensor of chemical species according to claim 10, wherein the concentration is in a range from 1000 ppm to 3000 ppm.

12. An optical sensor of chemical species according to claim 1, wherein the chalcogenide glass matrix of said fluorescent source of infrared radiation is doped with $Dy^{3+}$ or $Pr^{3+}$ ions at a concentration greater than or equal to 500 ppm, whereby said fluorescent source of in infrared radiation emits radiation at 4.3 µm.

13. An optical sensor of chemical species according to claim 12, wherein the concentration is in a range from 1000 ppm to 3000 ppm.

14. An optical sensor of chemical species according to claim 1, wherein said fluorescent source of infrared radiation presents emission with a spectrum width at half maximum lying in the range 200 nm to 800 nm.

15. An optical sensor of chemical species according to claim 1, wherein said fluorescent source of infrared radiation is in the form of a waveguide.

16. A method of detecting a chemical species by measuring the absorption at two or more distinct wavelengths of incoherent infrared radiation emitted by fluorescence from rare earth ions in a chalcogenide glass matrix, the method being characterized by the use of a sensor of chemical species according to claim 1.

17. A method according to claim 16, wherein:
   said incoherent infrared radiation presents a spectrum width at half maximum lying in the range 200 nm to 800 nm, and a wavelength of 4.3 µm; and
   said chemical species is gaseous $CO_2$.

18. An optical sensor of chemical species according to claim 1, wherein said or each fluorescent element is in the form of an optical fiber.

19. An optical sensor of chemical species according to claim 1, wherein said fluorescent source of infrared radiation is in the form of an optical fiber.

* * * * *